(12) United States Patent
Fitzpatrick et al.

(10) Patent No.: US 8,076,512 B2
(45) Date of Patent: Dec. 13, 2011

(54) PREPARATION OF ACETIC ACID

(75) Inventors: Michael E. Fitzpatrick, League City, TX (US); Chuc Tu Nguyen, Friendswood, TX (US); Wayne J. Brtko, Glen Mills, PA (US); Brian A. Salisbury, Oxford, PA (US)

(73) Assignees: Equistar Chemicals, L.P., Houston, TX (US); Lyondell Chemical Technology, Houston, TX (US)

( * ) Notice: Subject to any disclaimer, the term of this patent is extended or adjusted under 35 U.S.C. 154(b) by 203 days.

(21) Appl. No.: 12/583,871

(22) Filed: Aug. 27, 2009

(65) Prior Publication Data
US 2011/0054213 A1 Mar. 3, 2011

(51) Int. Cl.
*C07C 51/42* (2006.01)
*C07C 53/10* (2006.01)

(52) U.S. Cl. ......................................... 562/608; 562/607
(58) Field of Classification Search .................. None
See application file for complete search history.

(56) References Cited

U.S. PATENT DOCUMENTS

| 5,371,286 | A | * | 12/1994 | Blay et al. ..................... 562/519 |
| 5,416,237 | A | | 5/1995 | Aubigne et al. |
| 5,620,567 | A | * | 4/1997 | Seidel et al. .................... 203/34 |
| 5,817,869 | A | | 10/1998 | Hinnenkamp et al. |
| 5,932,764 | A | | 8/1999 | Morris et al. |
| 6,667,418 | B2 | | 12/2003 | Broussard et al. |
| 7,345,197 | B1 | | 3/2008 | Hallinan et al. |
| 7,485,749 | B2 | * | 2/2009 | Sawyer et al. ................ 562/608 |
| 7,524,988 | B2 | * | 4/2009 | Harris et al. .................. 562/608 |

* cited by examiner

*Primary Examiner* — Karl J Puttlitz

(57) ABSTRACT

A method for reducing aldehydes in an acetic acid production process is disclosed. The acetic acid is produced by reacting methanol and carbon monoxide in the presence of a carbonylation catalyst. The method comprises reacting an aldehyde-containing stream with an alcohol to form an acetal-containing stream. An acetal-enriched stream is separated from the acetal-containing stream and then hydrolyzed to form a hydrolysis mixture comprising the alcohol and the aldehydes. The alcohol is isolated from the hydrolysis mixture and used to react with the aldehyde-containing stream to form the acetal-containing stream. The invention reduces aldehydes in the acetic acid produced.

15 Claims, No Drawings

PREPARATION OF ACETIC ACID

FIELD OF THE INVENTION

The invention relates to preparation of acetic acid. More particularly, the invention relates to a method for producing acetic acid with a reduced level of aldehydes.

BACKGROUND OF THE INVENTION

Prior to 1970, acetic acid was made from methanol and carbon monoxide using cobalt catalysts. Rhodium catalysts, which were developed later by Monsanto, for acetic acid synthesis, are much more active than cobalt catalyst, thus allow lower reaction pressures and temperatures. Most importantly, the rhodium catalysts give high selectivities to acetic acid.

One problem with the original Monsanto process is that a large amount of water (about 14%) is needed to produce hydrogen in the reactor via the water-gas shift reaction. Water and hydrogen help to convert Rh(III) and Rh(II) species to the active Rh(I) species. The large amount of water increases the amount of hydrogen iodide present in the reaction system, which is highly corrosive. Further, removing a large amount of water from the acetic acid product is costly.

In the late 1970s, the Monsanto process was improved by including an iodide salt such as lithium iodide to the rhodium catalyst system. Lithium iodide increases the catalyst stability by minimizing the side reactions that produce inactive Rh(III) species and therefore the amount of water needed is reduced. However, the high concentration of lithium iodide promotes stress crack corrosion of the reactor vessels. Furthermore, the use of iodide salts increases the iodide impurities in the acetic acid product.

In the late 1990s, another rhodium carbonylation catalyst system was developed. The catalyst system uses a pentavalent Group VA oxide such as triphenylphosphine oxide as a catalyst stabilizer instead of an iodide salt. The catalyst system not only reduces the amount of water needed but also increases the carbonylation rate and acetic acid yield. See U.S. Pat. No. 5,817,869.

One challenge still facing the industry is that lowering water concentration in the methanol carbonylation results in increased aldehydes formation. Methods for removing aldehydes from acetic acid products are known. For instance, U.S. Pat. No. 6,667,418 discloses a method for reacting aldehydes impurities with air, hydrogen peroxide and other free radical initiators in an integrated acetic acid production process at an elevated temperature. Introducing free radical initiators in acetic acid production processes is undesirable because some free radical initiators are explosive and may present safety concerns. U.S. Pat. No. 7,345,197 discloses a method for removing aldehyde impurities from acetic acid that comprises extracting the aldehyde impurities from a methyl iodide solution such as the decanter heavy phase with a polyol. After the aldehyde impurities are removed, the methyl iodide heavy phase is recycled to the carbonylation reaction. U.S. Pat. No. 7,485,749 discloses another method for removing aldehyde impurities from an acetic acid stream in an acetic acid preparation process. The method comprises reacting aldehyde impurities with a hydroxyl compound in a drying distillation column or a combined column to form corresponding acetals. U.S. Pat. No. 7,524,988 discloses a method for preparing acetic acid comprising reacting a portion of the heavy, organic phase comprising mostly methyl iodide and aldehyde impurities with a hydroxyl compound to convert the aldehydes into acetals. The acetals are disposed of as waste.

There is a continued need for improved methods for producing acetic acid with low level of aldehydes.

SUMMARY OF THE INVENTION

The invention is a method for reducing aldehyde impurities from a stream in an acetic acid production processs by reacting methanol and carbon monoxide in the presence of a carbonylation catalyst. The method comprises reacting an aldehyde-containing stream with an alcohol to form an acetal-containing stream. An acetal-enriched stream is separated from the acetal-containing stream and then hydrolyzed to form a hydrolysis mixture comprising the alcohol and the aldehydes.

The alcohol is isolated from the hydrolysis mixture and used to react with the aldehyde-containing stream to form the acetal-containing stream.

DETAILED DESCRIPTION OF THE INVENTION

The present invention is a method for reducing aldehydes in an acetic acid production process. The acetic acid is produced by reacting methanol and carbon monoxide in the presence of a carbonylation catalyst. Suitable carbonylation catalysts include rhodium catalysts and iridium catalysts. Suitable rhodium catalysts are taught, for example, by U.S. Pat. No. 5,817,869. Suitable rhodium catalysts are formed from rhodium metal and rhodium compounds. Preferably, the rhodium compounds are selected from the group consisting of rhodium salts, rhodium oxides, to organo-rhodium compounds, coordination compounds of rhodium, the like, and mixtures thereof. More preferably, the rhodium compounds are selected from the group consisting of $Rh_2(CO)_4I_2$, $Rh_2(CO)_4Br_2$, $Rh_2(CO)_4Cl_2$, $Rh(CH_3CO_2)_2$, $Rh(CH_3CO_2)_3$, $HRh(CO)_2I_2$, the like, and mixtures thereof. Most preferably, the rhodium compounds are selected from the group consisting of $HRh(CO)_2I_2$, $Rh(CH_3CO_2)_2$, the like, and mixtures thereof.

Suitable iridium catalysts are taught, for example, by U.S. Pat. No. 5,932,764. Suitable iridium catalysts are formed from iridium metal or iridium compounds. Examples of suitable iridium compounds include $IrCl_3$, $IrI_3$, $IrBr_3$, $[Ir(CO)_2I]_2$, $[Ir(CO)_2Cl]_2$, $[Ir(CO)_2Br]_2$, $HIr(CO)_4I_2$, $HIr(CO)_2Br_2$, $HIr(CO)_2I_2$, $HIr(CH_3)I_3(CO)_2$, $Ir_4(CO)_{12}$, $Ir_3(CO)_{12}$, $Ir_2O_3$, $IrO_2$, $Ir(acac)(CO)_2$, $Ir(acac)_3$, $Ir(Ac)_3$, and $H_2IrCl_6$. Preferably, the iridium compounds are selected from the group consisting of iridium acetates, iridium acetylacetonates, the like, and mixtures thereof. More preferably, the iridium compounds are iridium acetates.

The iridium catalyst is preferably used with a co-catalyst. Preferred co-catalysts include metals and metal compounds selected from the group consisting of osmium, rhenium, ruthenium, cadmium, mercury, zinc, gallium, indium, and tungsten, their compounds, the like, and mixtures thereof. More preferred co-catalysts are selected from the group consisting of ruthenium compounds and osmium compounds. Most preferred co-catalysts are ruthenium compounds. Preferably, the co-catalysts are halogen-free compounds such as acetates.

The amount of catalyst used in the carbonylation reaction is generally 300 to 900 parts per million (ppm) of the reaction mixture.

The carbonylation reaction preferably uses a catalyst stabilizer. Suitable catalyst stabilizers include those known to the industry. In general, there are two types of catalyst stabilizers. The first type of catalyst stabilizer is an iodide salt such as lithium iodide. The second type of catalyst stabilizer is a non-salt stabilizer. Preferred non-salt stabilizers are pentavalent Group VA oxides. See U.S. Pat. No. 5,817,869. Phosphine oxides are more preferred. Triphenylphosphine oxides are most preferred. The amount of catalyst stabilizer used in the carbonylation reaction is generally 5 to 25 weight percent (wt %) of the reaction mixture, preferably 10 to 20 wt %.

The carbonylation reaction is preferably performed in the presence of water. Preferably, the concentration of water is from about 2 wt % to about 14 wt % based on the total weight of the reaction mixture. More preferably, the water concentration is from about 2 wt % to about 10 wt %. Most preferably, the water concentration is from about 4 wt % to about 8 wt %.

The carbonylation reaction is preferably performed in the presence of methyl acetate. Methyl acetate can be formed in situ. If desirable, methyl acetate can be added to the reaction mixture. Preferably, the concentration of methyl acetate is from about 2 wt % to about 20 wt % based on the total weight of the reaction mixture. More preferably, the concentration of methyl acetate is from about 2 wt % to about 16 wt %. Most preferably, the concentration of methyl acetate is from about 2 wt % to about 8 wt %.

The carbonylation reaction is preferably performed in the presence of methyl iodide. Methyl iodide is a catalyst promoter. Preferably, the concentration of methyl iodide is from about 0.6 wt % to about 36 wt % based on the total weight of the reaction mixture. More preferably, the concentration of methyl iodide is from about 4 wt % to about 24 wt %. Most preferably, the concentration of methyl iodide is from about 6 wt % to about 20 wt %. Alternatively, methyl iodide can be generated in the carbonylation reaction by adding hydrogen iodide.

Methanol and carbon monoxide are fed to the carbonylation reaction. It is believed that methanol does not react directly with carbon monoxide in the presence of the catalyst to form acetic acid. Instead, methanol is converted to methyl iodide by reacting with hydrogen iodide. Methyl iodide then reacts with carbon monoxide and water in the presence of the catalyst to form acetic acid and to regenerate the hydrogen iodide.

Hydrogen may also be fed into the reaction. Addition of hydrogen can enhance the carbonylation efficiency. Preferably, the concentration of hydrogen is from about 0.1 mole percent (mol %) to about 5 mol % relative to the amount of carbon monoxide in the reactor. More preferably, the concentration of hydrogen is from about 0.3 mol % to about 3 mol % relative to carbon monoxide.

The carbonylation reaction is preferably performed at a temperature within the range of about 150° C. to about 250° C. More preferably, the reaction is performed at a temperature within the range of about 150° C. to about 200° C. The carbonylation reaction is preferably performed under a pressure within the range of about 200 psig to about 2,000 psig. More preferably, the reaction is performed under a pressure within the range of about 300 psig to about 500 psig.

The carbonylation reaction produces a reaction mixture comprising acetic acid, carbon monoxide, the catalyst, aldehydes, and other components. The aldehydes are byproducts of the carbonylation reaction. Examples of aldehydes present in the reaction mixture include acetaldehyde, propionaldehyde, butyraldehydes, crotonaldehyde, their derivatives such as 2-ethyl crotonaldehyde, 2-ethyl butyraldehyde, and the like.

According to the invention, an aldehyde-containing stream is generated from the reaction mixture. At a least a portion of the aldehyde-containing stream is reacted with an alcohol to form an acetal-containing stream (acetal-forming step).

Examples of suitable alcohols for reacting with the aldehydes include $C_4$-$C_{10}$ mono alcohols, $C_2$-$C_{10}$ glycols, $C_3$-$C_{10}$ glycerins, and mixtures thereof. Glycols are preferred because they form stable cyclic acetals with aldehydes. Suitable glycols include 2-methyl-1,3-propanediol, ethylene glycol, 1,2-propylene glycol, 1,3-propylene glycol, 1,2-butanediol, 1,3-butanediol, 1,5-pentanediol, 1,6-hexanediol, 2,2-dimethyl-1,3-propanediol, cyclohexane-1,4-dimethanol, neopentyl glycol, the like, and mixtures thereof. Ethylene glycol and 2-methyl-1,3-propanediol are most preferred because they are inexpensive and readily available. The molar ratio of the alcohol used relative to the aldehydes present in the heavy phase is generally in the range of from 0.5:1 to 100:1, preferably from 1:1 to 10:1.

The reaction of the alcohol with the aldehyde-containing stream may preferably be performed in the presence of an acid. Suitable acids include hydrochloric acid, hydroiodic acid, nitric acid, phosphoric acid, sulfuric acid, acidic ion-exchange resins, the like, and mixtures thereof. The amount of acid used depends on the reaction conditions. Sulfonic resins are particularly preferred. When an acidic resin is used, the reaction of the alcohol with the heavy phase is preferably performed in a fixed-bed reactor at a temperature of 25 to 85° C.

The acetal-containing stream is separated to isolate an acetal-enriched stream. The acetal-containing stream is distilled to separate an acetal-enriched stream. The distillation may be performed under vacuum.

The acetal-enriched stream is reacted with water in the presence of an acid to form a hydrolysis mixture comprising the alcohol and aldehydes. Typically the molar ratio of water used relative to the acetals is from 1:1 to 100:1. The acids described in the previous section are suitable for the hydrolysis reaction. The alcohol is recovered by distillation from the reaction mixture and used in the acetal-forming step as described above.

Preferably, the carbonylation reaction uses, in addition to the carbonylation catalyst, a catalyst stabilizer, methyl iodide, water, and methyl acetate to produce a reaction mixture comprising acetic acid, carbon monoxide, the carbonylation catalyst, a catalyst stabilizer, methyl iodide, water, methyl acetate, and aldehydes.

At least a portion of the reaction mixture is separated by a flash separation into a liquid stream comprising the majority of the catalyst and the catalyst stabilizer, and a vapor stream comprising acetic acid, methanol, carbon monoxide, water, methyl iodide, and any other impurities generated during the carbonylation reaction including aldehydes. The liquid stream is then preferably recycled to the carbonylation reaction. The flash separation is preferably conducted at a pressure of from 15 to 30 psig and at a temperature of 110 to 140° C.

The vapor stream obtained from the flash separation is passed to a light-ends distillation. The light-ends distillation separates an overhead comprising methyl iodide, water, methyl acetate, and aldehydes from an acetic acid stream comprising mostly acetic acid, water, and minor amount of aldehydes. The light-ends distillation is typically operated at a temperature of 105 to 130° C. and a pressure of 15 to 25 psig.

Preferably, the acetic acid stream from the light-ends distillation column is passed to a drying column to remove water and then subjected to a heavy-ends distillation to remove the heavy impurities such as propionic acid, the remaining catalyst and catalyst stabilizer. A purified acetic acid is produced from the heavy-ends distillation. The heavy-ends distillation is typically operated at a temperature of 115 to 150° C. and a pressure of 5 to 15 psig.

A single column may be used in the place of the combination of the light-ends distillation and the drying column. The single column may vary in the diameter/height ratio and the number of stages according to the composition of vapor stream from the flash separation and the requisite product quality. For instance, U.S. Pat. No. 5,416,237, the teachings of which are incorporated herein by reference, discloses a single column distillation. In operation, the vapor stream from the flash separation is preferably introduced to the single column at the lower portion of the column, for instance, about 3 to 8 stages above the bottom of the column. A light stream, which comprises water, methyl iodide, and methyl acetate, is taken from the top portion of the single column. The light stream may be returned to the carbonylation reaction with or without further separation. An essentially anhydrous acetic acid (containing less than 1000 ppm water) is taken from the middle portion of the single column, for instance, about 10-20 stages from where the feed (i.e., vapor steam from the flash separation) enters the single column. A heavy stream, which may comprise the catalyst and the catalyst stabilizer carried over from the flash separation, is taken from the bottom of the single column. A single column distillation is particularly useful when the water concentration in the carbonylation is low, for instance, 6% or lower based on the total weight of the carbonylation reaction mixture. The overhead from the light-ends distillation or the single column distillation preferably is condensed and separated in a decanter to a light, aqueous phase and a heavy, organic phase. The heavy, organic phase comprises methyl iodide and aldehydes formed from the carbonylation reaction. The light, aqueous phase comprises water, acetic acid, and methyl acetate. At least a portion of the heavy phase is recycled to the carbonylation reactor. The light, aqueous phase is recycled to the carbonylation reactor, the light-ends distillation column, or the single column.

According to the present invention, a portion of the heavy organic phase is reacted with the alcohol to form an acetal-containing stream. The acetal-containing stream is distilled to separate a recovered methyl iodide stream from an acetal-enriched stream. The distillation is generally performed at a temperature of 100 to 150° C. and a pressure of 10 to 30 psig. The recovered methyl iodide stream, obtained as an overhead, generally contains about 60 to 95 wt % methyl iodide and may be recycled to the carbonylation reaction. The bottoms stream is an acetal-enriched stream. The distillation may also be performed under vacuum.

The acetal-enriched stream is reacted with water in the presence of an acid to form the aldehydes and the alcohol. The alcohol is recovered by distillation from the reaction mixture and used in the acetal-forming step as described above.

The invention removes aldehydes from the heavy phase before it is recycled to the carbonylation reaction, thus reduces the aldehydes traffic in the process. As a result, the acetic acid product contains a lower level of aldehydes. The alcohol is recovered by the hydrolysis reaction and reused in the process to reduce the consumption of alcohol.

We claim:

1. A method for reducing aldehydes from an acetic acid production process by reacting methanol and carbon monoxide in the presence of a carbonylation catalyst to produce at least one aldehyde-containing stream, said method comprising reacting the aldehyde-containing stream with an alcohol to form an acetal-containing stream, separating an acetal-enriched stream from the acetal-containing stream, hydrolyzing the acetal-enriched stream to form a hydrolysis mixture comprising the alcohol and the aldehydes, isolating the alcohol from the hydrolysis mixture, and recycling the alcohol to the acetal forming step.

2. The method of claim 1 wherein the alcohol is selected from the group consisting of $C_4$-$C_{10}$ mono-alcohols, $C_2$-$C_{10}$ glycols, $C_3$-$C_{10}$ glycerins, and mixtures thereof.

3. The method of claim 1, wherein the alcohol is a glycol selected from the group consisting of 2-methyl-1,3-propanediol, ethylene glycol, 1,2-propylene glycol, 1,3-propylene glycol, 1,2-butanediol, 1,3-butanediol, 1,5-pentanediol, 1,6-hexanediol, 2,2-dimethyl-1,3-propanediol, cyclohexane-1,4-dimethanol, neopentyl glycol, and mixtures thereof.

4. The method of claim 1, wherein the alcohol is 2-methyl-1,3-propanediol.

5. A method for producing acetic acid, said method comprising:
(a) reacting methanol and carbon monoxide in the presence of a carbonylation catalyst, a catalyst stabilizer, methyl iodide, water, and methyl acetate to produce a reaction mixture comprising acetic acid, water, methyl acetate, methyl iodide, the catalyst, the catalyst stabilizer, and aldehydes;
(b) flashing at least a portion of the reaction mixture to produce a vapor stream comprising acetic acid, water, methyl acetate, methyl iodide, and aldehydes and a liquid stream comprising the catalyst and the catalyst stabilizer;
(c) distilling the vapor stream to form an overhead stream comprising methyl iodide, water, acetic acid, methyl acetate, and aldehydes, and an acetic acid stream comprising acetic acid, aldehydes, and water;
(d) separating the overhead stream into a light aqueous phase comprising water and a heavy phase comprising methyl iodide and aldehydes;
(e) recycling the liquid stream and the heavy phase to step (a); wherein at least a portion of the aldehydes from the heavy phase is removed by the following steps:
(i) reacting at least a portion of the heavy phase with an alcohol to form an acetal-containing stream;
(ii) distilling the acetal-containing stream into a recovered methyl iodide stream and an acetal-enriched stream;
(iii) recycling the recovered methyl iodide stream to step (a);
(iv) hydrolyzing the acetal-enriched stream to form a hydrolysis mixture comprising the alcohol and the aldehydes; and
(v) isolating the alcohol from the hydrolysis mixture and recycling the alcohol to step (i).

6. The method of claim 5 further comprising purifying the acetic acid stream by a drying column distillation and a heavy-end column distillation to produce purified acetic acid.

7. The method of claim 5 wherein the alcohol is selected from the group consisting of $C_4$-$C_{10}$ mono-alcohols, $C_2$-$C_{10}$ glycols, $C_3$-$C_{10}$ glycerins, and mixtures thereof.

8. The method of claim 5, wherein the alcohol is a glycol selected from the group consisting of 2-methyl-1,3-propanediol, ethylene glycol, 1,2-propylene glycol, 1,3-propylene glycol, 1,2-butanediol, 1,3-butanediol, 1,5-pentanediol, 1,6-hexanediol, 2,2-dimethyl-1,3-propanediol, cyclohexane-1,4-dimethanol, neopentyl glycol, and mixtures thereof.

9. The method of claim 5, wherein the alcohol is 2-methyl-1,3-propanediol.

10. The method of claim 5, wherein the reaction between the heavy phase and the alcohol is performed in the presence of an acidic resin.

11. The method of claim 10, wherein the acidic resin is a sulfonic resin.

12. The method of claim 5, wherein the hydrolysis of the acetal-enriched stream is performed in the presence of an acidic resin.

13. The method of claim 12, wherein the acidic resin is a sulfonic resin.

14. The method of claim 5, wherein the catalyst stabilizer is a pentavalent Group VA oxide.

15. The method of claim 5, wherein the catalyst stabilizer is a phosphine oxide.

* * * * *